United States Patent [19]

Malsch et al.

[11] Patent Number: 5,626,724
[45] Date of Patent: May 6, 1997

[54] RECOVERY OF N-ETHYLPIPERAZINE BY DISTILLATION

[75] Inventors: Klaus-Dieter Malsch, Schifferstadt; Douglas Hutton, Limburgerhof; Ernst Lang, Wachenheim, all of Germany

[73] Assignee: BASF Aktiengesellschaft, Ludwigshafen, Germany

[21] Appl. No.: 510,562

[22] Filed: Aug. 2, 1995

[30] Foreign Application Priority Data

Aug. 3, 1994 [DE] Germany .................. 44 27 511.0

[51] Int. Cl.$^6$ .................. B01D 3/10; B01D 3/38
[52] U.S. Cl. .................. 203/76; 203/79; 203/92; 203/97; 544/404
[58] Field of Search .................. 203/71, 73, 76, 203/79, 92, 97; 544/404

[56] References Cited

U.S. PATENT DOCUMENTS

| | | | |
|---|---|---|---|
| 3,126,383 | 3/1964 | Cooper | 544/404 |
| 3,154,552 | 10/1964 | Weipert et al. | 544/404 |
| 4,736,030 | 4/1988 | Mueller et al. | 544/374 |
| 4,911,793 | 3/1990 | Mueller et al. | 203/92 |

*Primary Examiner*—Nina Bhat
*Attorney, Agent, or Firm*—Keil & Weinkauf

[57] ABSTRACT

In a process for the recovery of N-ethylpiperazine by distillation from mixtures with N,N'-diethylpiperazine, piperazine, ethanol, water and accompanying substances, water is added in a manner such that, at the location of the addition of the water, the piperazine concentration is greater than the N-ethylpiperazine concentration. The water may be added to the reflux to the top of the column.

4 Claims, No Drawings

RECOVERY OF N-ETHYLPIPERAZINE BY DISTILLATION

The present invention relates to a process for the recovery of N-ethylpiperazine by distillation from mixtures with piperazine, N,N'-diethylpiperazine, water and minor amounts of ethanol and other components.

N-Ethylpiperazine is an important intermediate for organic syntheses which is prepared in industry by various known processes from ethanol and piperazine. These usually give mixtures which, in addition to N-ethylpiperazine, contain the less desirable N,N'-diethylpiperazine, unconverted piperazine, excess ethanol, water and minor amounts of some byproducts.

As is generally known and is disclosed in EP-A-181 536 and EP-B1-302 440, working up the abovementioned mixtures presents considerable difficulties which are due to the presence of piperazine and N,N'diethylpiperazine. According to EP-B1-302 440, the difficulties in the separation of the mixtures by distillation are overcome by carrying out the distillation under certain conditions in the presence of a defined amount of water in the still, making it possible to remove N,N'-diethylpiperazine from the starting material before the piperazine by batchwise distillation.

However, this known process is not completely satisfactory since the piperazine separated off solidifies on condensation and blocks the condensation apparatuses. Furthermore, with the addition of water to the still, ethylpiperazine too is taken off via the top and is thus lost; moreover, too large an amount of energy is required.

It is an object of the present invention to prevent the solidification of the piperazine in the condensation apparatus during the separation of N-ethylpiperazine from the mixtures described above by distillation and to avoid a substantial increase in the N-ethylpiperazine concentration in the piperazine fraction and at the same time to keep the energy consumption low.

We have found that this object is achieved, according to the invention, if, while the piperazine fraction is being separated off, water is added at a location where the piperazine concentration is greater than the N-ethylpiperazine concentration; preferably, the water is added to the reflux to the top of the column. In a particular advantageous embodiment of the novel process, the amount of water is from 10 to 40% by weight, based on the amount flowing out of the condenser.

The novel process is based on the surprising observation that, on the one hand, water depresses the melting point of piperazine to such an extent that the piperazine does not solidify in the condensation apparatus and, on the other hand, that the addition of water to the reflux does not lead to any substantial increase in the N-ethylpiperazine concentration in the piperazine fraction.

The starting mixtures are obtained in the ethylation of piperazine with ethanol, which is known in different process variants. These reactions are carried out in the presence of hydrogenation catalysts and hydrogen, frequently also in the presence of water and mineral bases, the ethanol advantageously being used in excess relative to the piperazine.

After the solid hydrogenation catalyst has been separated off, the excess ethanol is distilled off together with small amounts of water. The mixture thus obtained consists, per 100 kg, of:

30-85 kg of N-ethylpiperazine
7-40 kg of N,N'-diethylpiperazine
3-20 kg of piperazine
0-40 kg of water
0-5 kg of ethanol
0-5 kg of accompanying substances.

This is the starting mixture of the novel process. According to EP-A-302 440, a defined amount of water is added to said starting mixture, and N,N'-diethylpiperazine is separated off, except for small amounts. The remaining mixture consists, per 100 kg, of:

50-90 kg of N-ethylpiperazine
3-15 kg of N,N'-diethylpiperazine
4-30 kg of piperazine
0-10 kg of water
0-7 kg of accompanying substances.

In the stepwise distillation of this mixture, a forerun comprising water, piperazine and small amounts of N-ethylpiperazine is obtained in the first distillation step, which begins at about 98° C. During this distillation step, the water concentration gradually decreases while the piperazine concentration and, to a small extent, the N-ethylpiperazine concentration increases.

In the subsequent second distillation step, which follows at a still temperature of about 150° C., water is added, according to the invention, to the reflux. A fraction which consists essentially of piperazine, water and small amounts of N-ethylpiperazine is obtained.

In the third distillation step, pure N-ethylpiperazine is removed by distillation at 155° C. A bottom fraction which contains N,N'-diethylpiperazine and other high-boiling components remains behind.

The number of theoretical plates required for separating the four fractions is advantageously from 15 to 60, preferably from 20 to 50. Recommended reflux ratios are 0.5-2 (1st step), 5-20 (2nd step) and 2-5 (3rd step).

The third distillation step may be preceded by an intermediate cut. In the intermediate cut, which begins at about 155° C., residual amounts of piperazine and water are removed together with N-ethylpiperazine. The N-ethylpiperazine contained in the intermediate cut can be recovered, for example, by working up the intermediate cut together with the next batch by distillation. The intermediate cut is operated at a reflux ratio of 20-50.

All data above apply to the procedure under atmospheric pressure (about 1 bar), but the entire distillation or individual distillation steps may readily be carried out at reduced or superatmospheric pressure, for example at from 0.05 to 10 bar, since the separation behavior of the starting mixtures and the mixtures formed from time to time from them does not change radically in this range.

The novel process can also be designed as a continuous process, the number of theoretical plates required for the procedure under atmospheric pressure in the rectifying section being about 10-30 for the first step, about 20-50 for the second step and about 5-20 for the third step. About 10-15 theoretical plates are sufficient for all steps in the stripping section.

In terms of apparatus, the novel process presents no problems and can therefore be carried out in the usual manner in columns of any design, including, for economic reasons, preferably packed columns or columns having a stacked packing.

Since the object of fractionating piperazine-containing reaction mixtures and obtaining the N-ethylpiperazine in pure form is successfully achieved by the novel process, it is no longer necessary to allow the piperazine to undergo substantial reaction in the synthesis step. This makes it possible to reduce the amount of undesirable N,N'-diethylpiperazine to a minimum in economic terms. In addition, the energy and time required for recovering N-ethylpiperazine are substantially reduced.

The novel process is to be illustrated in detail below with reference to an example.

1000 g of a starting mixture consisting of 740 g of N-ethylpiperazine 110 g of N,N'-diethylpiperazine 110 g of piperazine 40 g of water are subjected to fractional distillation in a packed column having about 20 theoretical plates at 1 bar. This is effected in the following stages:

1st stage 45 g of a fraction containing <0.1% by weight of N,N'-diethylpiperazine, 3% by weight of N-ethylpiperazine, 78% by weight of water and 16% by weight of piperazine are taken off at from 98° to 150° C. The reflux ratio is 1.

2nd stage 230 g of a fraction containing <0.1% by weight of N,N'-diethylpiperazine, 9% by weight of N-ethylpiperazine, 12% by weight of water and 78% by weight of piperazine are taken off at from 150° to 155° C. 20 g of water are added to the reflux, distributed uniformly over the distillation step. The reflux ratio is 10.

3rd stage 80 g of a fraction containing <0.1% by weight of N,N'-diethylpiperazine, <0.1% by weight of water, 3% by weight of piperazine and 97% by weight of N-ethylpiperazine are taken off at from 155° to 160° C. The reflux ratio is 30.

4th stage 490 g of a fraction containing >99% by weight of N-ethylpiperazine are taken off at 160° C. The reflux ratio is 3.

By means of this procedure, 66% of the N-ethylpiperazine used can be recovered as pure product. A further 10% can be recycled and worked up with the next batch.

We claim:

1. A process for the recovery of N-ethylpiperazine by distillation from mixtures with N,N'-diethylpiperazine, piperazine, ethanol, water and accompanying substances in a distillation column having a still, trays or packings and at its top a condenser for producing reflux, wherein, a stepwise distillation of the mixture proceeds as follows:

a) in the first distillation step at about 98° C., a forerun comprising water, piperazine and small amounts of N-ethypiperazine is obtained;

b) in the subsequent second distillation step at about 150° C., water is added to the reflux and a fraction of piperazine, water and small amounts of N-ethylpiperazine is obtained;

c) in the third distillation step at 155° C. pure N-ethylpiperazine is removed; leaving a bottom fraction which contains N,N'-diethylpiperazine and other high-boiling components.

2. A process as claimed in claim 1, wherein the amount of water is from 10 to 40% by weight, based on the amount flowing out of the condenser at the top of the distillation column.

3. A process as claimed in claim 1, wherein the piperazine fraction is separated off at a temperature of from about 145° to 155° C. at about 1 bar.

4. A process as claimed in claim 1, wherein, after the main amount of the piperazine has been separated off and before the N-ethylpiperazine has been separated off, an intermediate distillation step or cut is provided in which residual amounts of piperazine and water are removed together with N-ethylpiperazine and the mixture obtained in this intermediate cut is worked up with the next batch by distillation.

* * * * *

UNITED STATES PATENT AND TRADEMARK OFFICE
CERTIFICATE OF CORRECTION

PATENT NO. : 5,626,724
DATED : May 6, 1997
INVENTOR(S) : MALSCH et al.

It is certified that error appears in the above-indentified patent and that said Letters Patent is hereby corrected as shown below:

Column 4, claim 1, line 11, "N-ethypiperazine" should be --N-ethylpiperazine--.

Signed and Sealed this

Eighth Day of July, 1997

*Attest:*

BRUCE LEHMAN

*Attesting Officer*     *Commissioner of Patents and Trademarks*